US012746030B2

(12) United States Patent
Paulo Portinha et al.

(10) Patent No.: US 12,746,030 B2
(45) Date of Patent: Sep. 29, 2026

(54) EXTRACTION TOOL

(71) Applicant: SAÚDE VIÁVEL S.A., Oporto (PT)

(72) Inventors: Carlos Jorge Paulo Portinha, Oporto (PT); Tiago José Arieira Esteves, Oporto (PT)

(73) Assignee: SAÚDE VIÁVEL S.A., Oporto (PT)

( * ) Notice: Subject to any disclaimer, the term of this patent is extended or adjusted under 35 U.S.C. 154(b) by 127 days.

(21) Appl. No.: 18/868,901

(22) PCT Filed: May 24, 2023

(86) PCT No.: PCT/IB2023/055349
§ 371 (c)(1),
(2) Date: Nov. 25, 2024

(87) PCT Pub. No.: WO2023/228112
PCT Pub. Date: Nov. 30, 2023

(65) Prior Publication Data
US 2026/0191554 A1 Jul. 9, 2026

(30) Foreign Application Priority Data
May 25, 2022 (PT) .......................................... 117996

(51) Int. Cl.
*A61B 17/3205* (2006.01)
*A61B 17/00* (2006.01)

(52) U.S. Cl.
CPC ................... *A61B 17/32053* (2013.01); *A61B 2017/00752* (2013.01)

(58) Field of Classification Search
CPC .......... A61B 17/32053; A61B 17/3205; A61B 17/322; A61B 17/32; A61B 2017/3225; A61B 2017/00752; A61B 2018/00476
(Continued)

(56) References Cited

U.S. PATENT DOCUMENTS 5,827,297 A * 10/1998 Boudjema .......... A61B 17/3417 600/564
2004/0143275 A1 * 7/2004 Chen ................. A61M 37/0076 606/133
(Continued)

FOREIGN PATENT DOCUMENTS

JP 2007229330 A 9/2007
WO 2015186146 A1 12/2015
(Continued)

OTHER PUBLICATIONS

International Search Report and Written Opinion of the International Searching Authority, mailed on Aug. 22, 2023, issued for the corresponding International Application No. PCT/IB2023/055349, 12 pages.

*Primary Examiner* — Dianne Dornbusch
(74) *Attorney, Agent, or Firm* — LUCAS & MERCANTI, LLP

(57) ABSTRACT

An extraction tool configured to, by control provided by an operator, autonomously pierce a skin surface, detach and aspirate a follicular unit therein included to a storage location. The proposed extraction tool allows to extract a follicular unit in a perpendicular or a non-perpendicular positioning with regard to the skin surface plane, as well performing counting of the aspirated detached follicular units based on a behavioral analysis of the motor comprised in the extraction tool.

15 Claims, 16 Drawing Sheets

(58) Field of Classification Search
USPC .......................................................... 606/133
See application file for complete search history.

(56) References Cited

U.S. PATENT DOCUMENTS

| | | | | |
|---|---|---|---|---|
| 2010/0125287 | A1* | 5/2010 | Cole ................ | A61B 17/32053 606/133 |
| 2014/0031839 | A1* | 1/2014 | Umar ..................... | A45D 26/00 606/133 |
| 2018/0325544 | A1* | 11/2018 | Park ................. | A61B 17/32053 |
| 2020/0046399 | A1* | 2/2020 | Park ................. | A61B 17/32053 |

FOREIGN PATENT DOCUMENTS

| | | | |
|---|---|---|---|
| WO | 2016042579 | A2 | 3/2016 |
| WO | 2019241247 | A1 | 12/2019 |

* cited by examiner

EXTRACTION TOOL

CROSS-REFERENCE TO RELATED APPLICATION

This application is a 371 of PCT/IB2023/055349, filed May 24, 2023, which claims the priority from Portugal Patent Application No. 117996, filed May 25, 2022, the contents of each of which are incorporated herein by reference

TECHNICAL FIELD

The present application describes an extraction tool configured to, by control means provided by an operator, autonomously pierce a skin surface, detach and aspirate a follicular unit therein included to a storage location.

BACKGROUND ART

According to the known current state of the art, the existing extraction tools do not allow the extraction of follicular units aligned with the rotation axis of the extraction tool. The devices developed so far include a rotation movement but where the follicular extraction process uses an inclination angle in relation to the patient's skin surface, precisely because of the difficulty in guaranteeing the alignment between the rotating punch and the respective extraction.

Document WO2019241247A1 discloses a system, method, and apparatus for harvesting follicular units from an epidermis. The disclosed apparatus includes a hollow tubular structure having a central axis and an end structure that is attached to an end of the hollow tubular structure. The end structure terminates distally at a substantially flat annular face that is substantially in a plane perpendicular to the central axis. The flat annular face has a sharp outer edge.

SUMMARY

The present invention describes an extraction tool to pierce a skin surface, detach and aspirate a follicular unit therein enclosed, comprising at least a motor, a circular hollow section punch and a rotary union; the motor comprises a central rotating shaft with two ends which extends beyond the dimensions of said motor at least in one first end and which will be mechanically adapted to the circular hollow section punch through a coupler; and the rotary union, comprising a first end and a second end, is coupled by its first end to the motor through the second end of the central rotating shaft, through a rear flange adapted to an outer structure of the motor and through a rotary union fixation cover that promotes the fitting and positioning of the rotary union against said outer structure of the motor; the second end of rotary union is connected to a control unit through an Outer PTFE tube; and the motor is connected to said control unit through energy and control cabling; the control unit being configured to control at least a rotation procedure of the circular hollow section punch during the skin surface piercing and detachment of a follicular unit therein enclosed and aspirate the detached follicular unit through the circular hollow punch section comprised therein towards the control unit.

In a proposed embodiment of present invention, the circular hollow section punch is mechanically adapted to the coupler at least by means of a circular hollow section shaft, a hollow section collet and a hollow section compression nut sequentially fitted together.

Yet in another proposed embodiment of present invention, the central rotating shaft comprises a circular hollow section between the two ends extending beyond the dimensions of said motor at least in one first end.

Yet in another proposed embodiment of present invention, the rotary union is composed by an inferior shell and an upper shell, both of said shells comprising a circular hollow section with independent bearings which are fitted to a shaft to ensure independent movement between both of said shells.

Yet in another proposed embodiment of present invention, the upper shell comprises a barbed section and a threaded section configured to fit the Outer PTFE tube through a tube threaded lock.

Yet in another proposed embodiment of present invention, the shaft comprises a threaded section and a barbed section.

Yet in another proposed embodiment of present invention, the barbed section of the shaft and the barbed section of the upper shell rotate independently from each other and are internally connected through a circular hollow section.

Yet in another proposed embodiment of present invention, the circular hollow section punch comprises a knurled section and a barbed section.

Yet in another proposed embodiment of present invention, the circular hollow section punch comprises a hollow piercing section of cylindrical shape, said section comprising a first linearly cylindrical portion with constant diameter, and a second cylindrical portion with linearly converging diameter towards the knurled section resulting in a convergence angle with regard to a rotation axis of the punch.

Yet in another proposed embodiment of present invention, the extraction tool comprises an inner PTFE tube with a first end fitted to the barbed section of the circular hollow section punch, and a second end fitted to the barbed section of the shaft, ensuring an internal hollow circuit between the knurled section and a follicle reservoir comprised in the control unit.

Yet in another proposed embodiment of present invention, the rotation procedure of the circular hollow section punch is provided by the rotation of the central rotating shaft therein coupled and which comprises a left or a right rotation with adjustable continuous rotational velocity.

The present invention further describes a method of operating the extraction tool previously described, characterized by the control unit comprising the control of the rotation velocity and rotation direction of the central rotating shaft of the motor; and the monitoring of a set of electrical and/or data parameters in order to determine errors or faults that lead to unsafe or suboptimal performance of the extraction procedure comprising the skin surface piercing and detachment of a follicular unit therein enclosed and aspirating the detached follicular unit.

In a proposed embodiment of the present method, the control unit performs the counting of the aspirated detached follicular units based on a behavioral analysis of the motor electrical and/or data parameters in response to the extraction procedure.

In a proposed embodiment of the present method, the extraction procedure comprises perpendicular positioning of the punch with regard to the skin surface plane while ensuring adjacent and parallel alignment between the follicular unit and the punch.

In a proposed embodiment of the present method, extraction procedure comprises non-perpendicular positioning of the punch with regard to the skin surface plane while ensuring adjacent and parallel alignment between the follicular unit and the punch.

GENERAL DESCRIPTION

The present application describes an extraction tool configured to, by control means provided by an operator, pierce a skin surface, detach and aspirate a follicular unit therein included to a storage location.

The tool, usually designated by Hair Follicle Extraction Tool, is suited for Follicular Unit Extraction (FUE) in a hair transplant procedure. To pierce the skin surface of a patient, the herein proposed extraction tool comprises a punch that operates as a cutting accessory, said punch may vary in size, mainly length, cutting profile and diameter. A wide array of sizes and dimensions is available in order to fit the patient assessment, said selection of the most appropriated accessory being selected preferably under supervision of a medical practitioner. An additional feature of the herein proposed extraction tool is associated with the inclusion of a rotational feature, which can be selected and/or adjusted in terms of rotational speed (in RPM) by the tool operator/medical practitioner. Additionally, said tool is also configured to promote the extraction of the follicular units by means of a suction process, and also perform the counting of the extracted units. The follicular unit to be extracted will be perfectly aligned with the extraction/rotation axis of the punching tool, which will promote its subsequent aspiration. The disclosed tool comprises an all-internal hollow section aligned within the rotating shaft axis, allowing the extracted follicular units to pass through it directly to the storage unit. Incorporated in the tool there is also an alarm system that monitors a set of parameters in order to detect errors, faults and actions that could lead to an unsafe or suboptimal performance of the extraction procedure. In case of any of the aforementioned situations are detected, the alarm system indicates visual and/or audible warnings, further identifying the fault condition that set the alarm. The procedure alarm thresholds are locally defined by the tool operator, while the device tool alarm thresholds are factory-set. The settings of the tool define the parameters that might be altered by the operator, such as velocity, suction, saline solution alarm.

The proposed suction system incorporated in the extraction tool, is supported by a refrigerated saline solution which prevents the extracted follicular units to be in contact with environment air for long periods. From the point of the procedure where the skin surface starts to bleed, the follicle unit (FU) and a small amount of soft tissue surrounding the follicle unit also flows within the system inwardly directed to the storage unit. The follicle units are eventually stored in a recipient or container, while the aforementioned fluids might still flow within the closed suction system. The previously cited saline solution is supplied by a flow circuit consisting of a recipient arrangement connected to a suction pump that ensures continuous closed-circuit movement of the solution.

The extraction tool is therefore a rotating tool that allows the attachment of a cutting tip (punch) with the purpose of perforating a skin layer to perform a hair transplant. The tool comprises a set of rotating elements, all of which are mechanically connected to the motor rotating shaft, which by its nature is responsible for ensuring the rotation movement of the tip of the extraction tool, i.e., the punch. The static elements of the extraction tool mainly comprise the outer covers and an outer tube fixation system through which the follicular units will be aspirated. The proposed arrangement and combination of elements, allow to overcome some of the previously mentioned functionality problems of the state-of-the-art mechanisms, resulting therefore in a unique solution.

The use of a rotary union, a coupler and a hollow shaft is part of the successful combination of the present invention. The rotary union is characterized by comprising a rotary section and a static section (in relation to the external structure of the extraction tool), and allows the follicular units to be extracted in an aligned manner (aligned within the same rotation axis of the rotating punch) with the rotary shaft of the motor, allowing them to be aspirated through the interior of said shaft, going through its entire interior, by means of connecting tubes, and exiting through the rear part of the rotary union which is static in relation to the external structure of the tool. Without the mechanical feature of the rotary union, the connection of the internal tube at the rear of the motor shaft would not be possible as the tube would wind up (following the rotation of the motor), preventing the tool from functioning correctly. The coupling of the upper section of the rotary union to the external structure of the tool therefore solves this problem, providing a swivelling solution. This improvement makes it possible to handle the extraction tool in a more natural way for the operator, and effective in terms of performance as it does not damage the structure of the follicular units extracted.

The mechanical coupling between the coupling element and the shaft of the motor provides freedom in the positioning of the punch, allowing its distance adjustment with regard to the motor, and therefore, allowing the length of the rotation axis to be adjusted. A shorter distance between the punch and the motor shaft results in a smaller extraction tool. In turn, increasing the distance between the punch and the motor shaft provides a longer extraction tool, and consequently thinner at its end. There are operational advantages and disadvantages to both approaches, related to the accuracy and stability of the extraction tool when operated by medical personnel. Also, this shaft is what "receives" the punch and transmits the rotation to it so that it can perforate the skin surface. It also allows adapting several different types of punches, with different shapes, sizes, cutting edges, and this plurality of options becomes an advantage compared to the market that has tools for a single type of punch that does not allow its replacement.

Another innovative approach of the present extraction tool is related to the fact that none of the known technologies currently comprise the current functional approach. The rotary shaft of the motor comprises a completely hollow section, the front shaft and coupler are hollow, the rotary union at the back is hollow; making it possible to place a tube between the punch and the extraction tool outlet, providing an internal path on the motor where the follicles will run by the application of a suction force during the cutting movement. All this procedure happens in line with the tool (aspiration aligned within the same axis of the rotation of the motor and the punch), allowing the operator to use the tool normally with the advantage that the follicular units at the same time that they are "cut/detached from the skin" are sucked and pass through the inside of the tool until they reach the back tube that then takes the follicular units to a tank.

Finally, functions such as rotation speed control, suction level control, automatic counting of the follicle units by measuring the current consumed by the motor, clogged tool detection, etc., are also provided by the current tool.

BRIEF DESCRIPTION OF THE DRAWINGS

For better understanding of the present application, figures representing preferred embodiments are herein attached which, however, are not intended to limit the technique disclosed herein.

DESCRIPTION OF EMBODIMENTS

Figure 1:
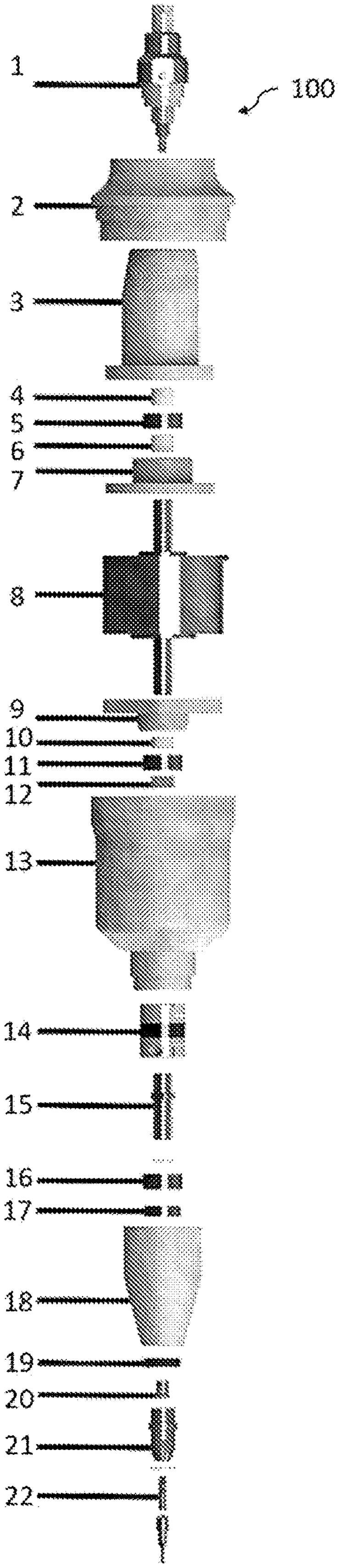
FIG. 1—illustrates a possible arrangement of the extraction tool (100) in an exploded view wherein the reference numbers refer to: 1. Rotary Union; 2. Rear cover; 3. Rotary Union Fixation Cover; 4. Rear motor bearing stopper 1; 5. Rear shaft bearing; 6. Rear motor bearing stopper 2; 7. Rear Flange; 8. Motor; 9. Front Flange; 10. Front motor bearing stopper 1; 11. Front shaft bearing; 12. Front motor bearing stopper 2; 13. Intermediate cover; 14. Coupler; 15. Shaft; 16. Shaft bearing; 17. Nut bearing; 18. Frontal cover; 19. Nut seal; 20. Collet; 21. Compression Nut; 22. Punch.

With reference to the figures, some embodiments are now described in more detail, which are however not intended to limit the scope of the present application.

The unique design and operation of the extraction tool (100) allows the passage of the skin extracted follicle units to be aspirated in a way aligned with the punch (22), passing throughout an existing hollow section along the entire length of the tool (100), passing through the motor (8) through its hollow shaft (25), and through which the connection between the punch (22) and the Outer PTFE tube (24) is ensured through an Inner PTFE tube (23). In addition to the suction system to allow the passage of the extracted follicle units, the Inner PTFE tube (23) comprises biocompatible features. The connection between the punch (22) and the rotary union (1) and the connection between the Outer PTFE tube (24) and the rotary union (1), and additionally the Follicle Reservoir (203) are also provided with biocompatible compliance. The rotation transmission between the motor (8) and the cutting tip—punch (8)—is done by means of a hollow shaft coupler (14). In addition, the alignment of the rotation axis of the extraction tool (100) is reinforced by means of multiple bearings, which ensure a uniform and stable speed delivery to the punch (22). The control of the speed and rotation force of the motor (8) is real-time monitored through by measuring parameters of the current consumed through the control unit (200), which also monitors the follicular unit count.

The extraction tool (100) comprises a sequence of coupling parts which are particularly designed and adapted for the purpose of the present invention which enable the synergetic effect described herein and proposed to be obtained. The sequence of elements comprised in the extraction tool (100) illustrated in FIG. 1 (in its exploded version), comprises then, in one of the proposed embodiments of the disclosed invention, a Rotary Union (1), a Rear cover (2), a Rotary Union Fixation Cover (3), a Rear motor bearing stopper 1 (4), Rear shaft bearing (5), Rear motor bearing stopper 2 (6), Rear Flange (7), a Motor (8), a Front Flange (9), a Front motor bearing stopper (10), a Front shaft bearing (11), a Front motor bearing stopper 2 (12), an Intermediate cover (13), a Coupler (14), a Shaft (15), a Shaft bearing (16), a Nut bearing (17), a Frontal cover (18), a Nut seal (19), a Collet (20), a Nut (21) and a Punch (22).

Figure 7:
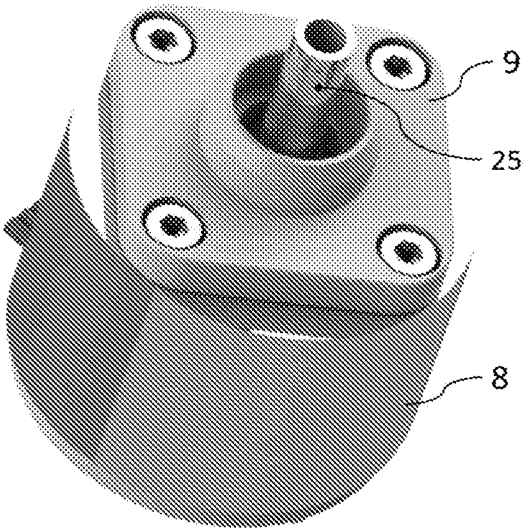
FIG. 7—illustrates a possible arrangement of the extraction tool (100) wherein the reference numbers refer to: 8. Motor; 9. Front Flange; 25. central hollow motor shaft.
Figure 8:
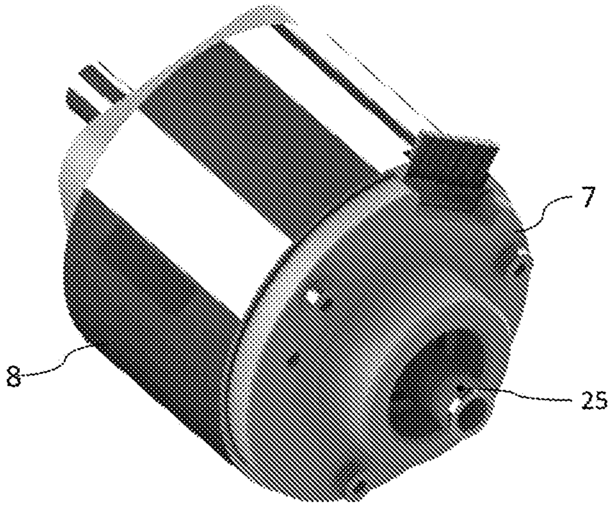
FIG. 8—illustrates a possible arrangement of the extraction tool (100) wherein the reference numbers refer to: 7. Rear Flange; 8. Motor; 25. central hollow motor shaft.
Figure 9:
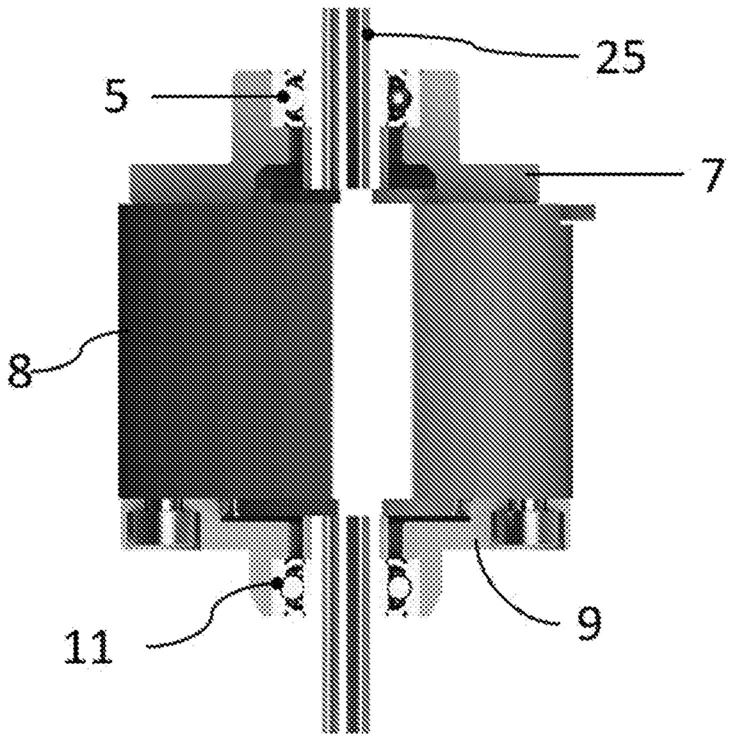
FIG. 9—illustrates a possible arrangement of the extraction tool (100) wherein the reference numbers refer to: 5. Rear shaft bearing; 7. Rear Flange; 8. Motor; 9. Front Flange; 11. Front shaft bearing; 25. central hollow motor shaft.
Figure 10:
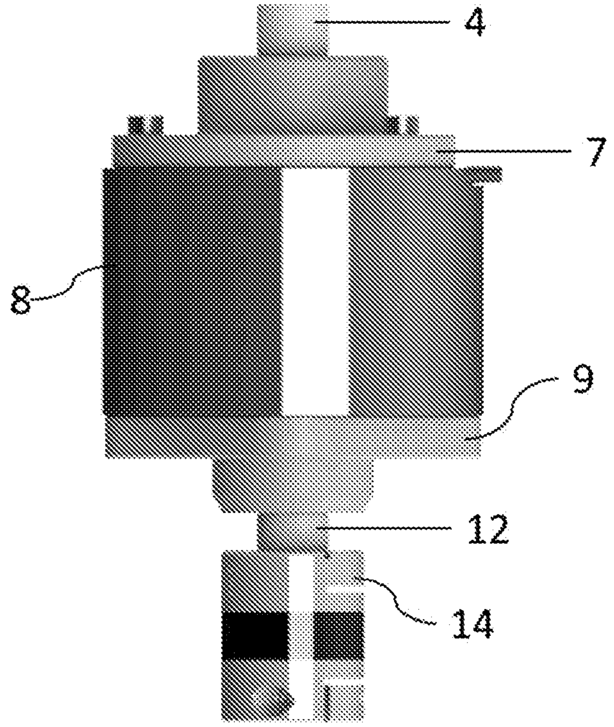
FIG. 10—Illustrates a Possible Arrangement of the extraction tool (100) wherein the reference numbers refer to: 4. Rear motor bearing stopper 1; 7. Rear Flange; 8. Motor; 9. Front Flange; 10. Front motor bearing stopper 1; 14. Coupler.
Figure 11:
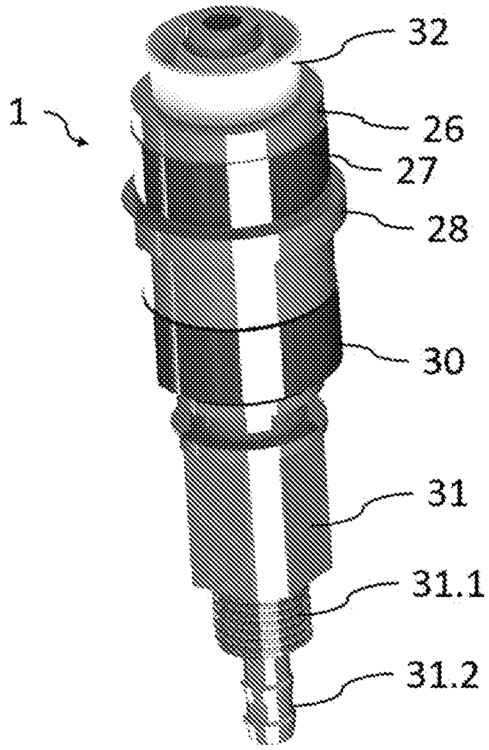
FIG. 11—Illustrates a Possible Arrangement of the extraction tool (100) wherein the reference numbers refer to: 1. Rotary Union; 26. Spacer; 27. Bearing; 28. Spacer; 30. Bearing; 31. Threaded shaft with barbed connection; 31.1. Threaded section of shaft (31); 31.2. Barbed section of shaft (31); 32. Seal.
Figure 12:
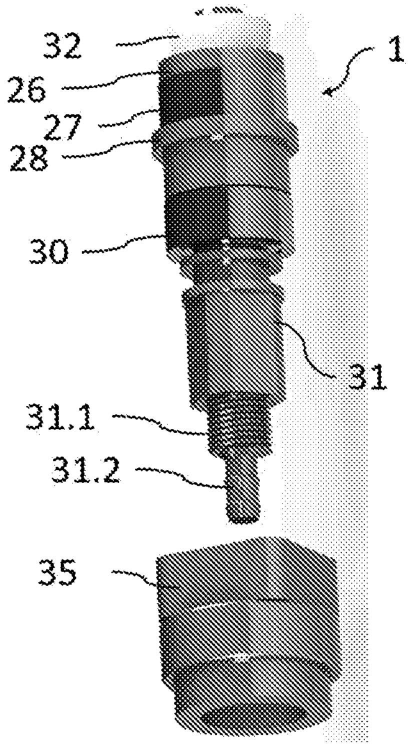
FIG. 12—Illustrates a Possible Arrangement of the extraction tool (100) wherein the reference numbers refer to: 1. Rotary Union; 26. Spacer; 27. Bearing; 28. Spacer; 30. Bearing; 31. Threaded shaft with barbed connection; 31.1. Threaded section of shaft (31); 31.2. Barbed section of shaft (31); 32. Seal; 35. Inferior Shell (outer body).
Figure 13:
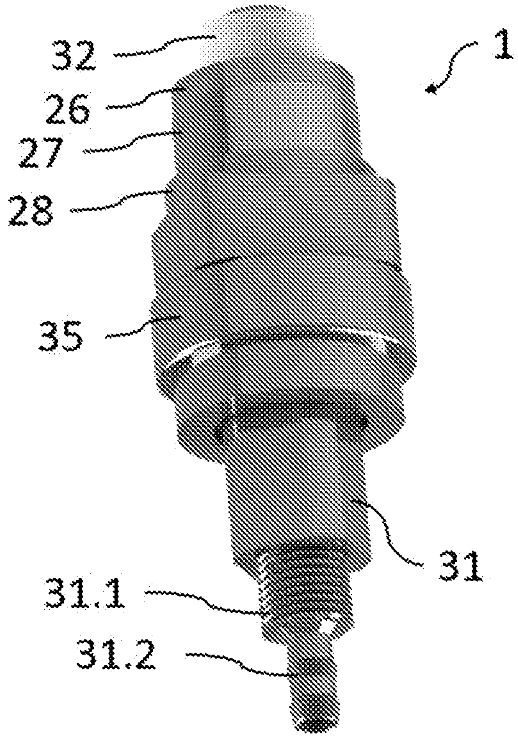
FIG. 13—Illustrates a Possible Arrangement of the extraction tool (100) wherein the reference numbers refer to: 1. Rotary Union; 26. Spacer; 27. Bearing; 28. Spacer; 31. Threaded shaft with barbed connection; 31.1. Threaded section of shaft (31); 31.2. Barbed section of shaft (31); 32. Seal; 35. Inferior Shell (outer body).
Figure 14:
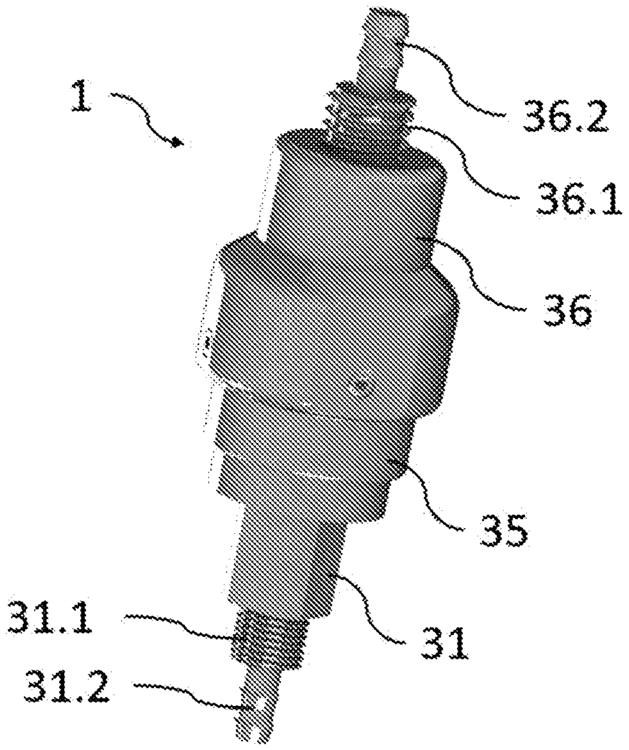
FIG. 14—Illustrates a Possible Arrangement of the extraction tool (100) wherein the reference numbers refer to: 1. Rotary Union; 31. Threaded shaft with barbed connection; 31.1. Threaded section of shaft (31); 31.2. Barbed section of shaft (31); 35. Inferior shell (outer body); 36. Upper shell (outer body); 36.1. Threaded section of upper shell (36); 36.2. Barbed section of upper shell (36).
Figure 15:
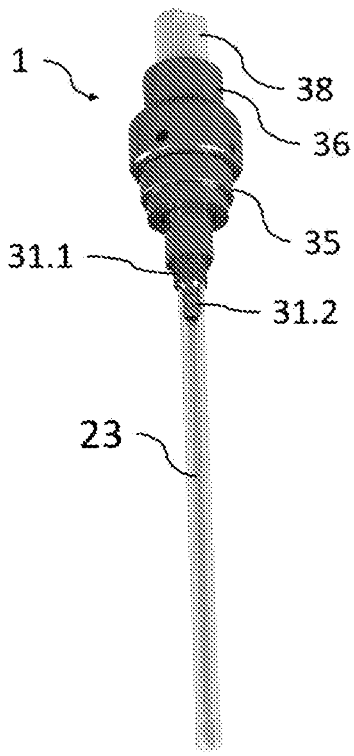
FIG. 15—Illustrates a Possible Arrangement of the extraction tool (100) wherein the reference numbers refer to: 1. Rotary Union; 23. Inner PTFE tube; 33. threaded section; 34. barbed section; 35. Inferior shell (outer body); 36. Upper shell (outer body); 38. Tube threaded lock.
Figure 16:
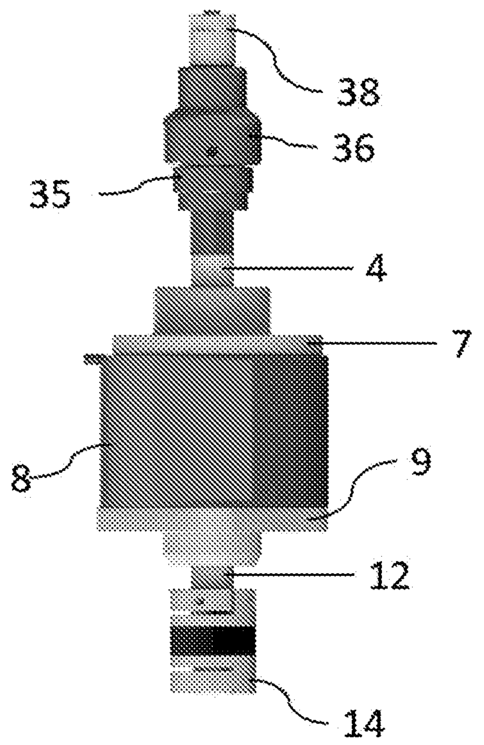
FIG. 16—Illustrates a Possible Arrangement of the extraction tool (100) wherein the reference numbers refer to: 4. Rear motor bearing stopper 1; 7. Rear Flange; 8. Motor; 9. Front Flange; 12. Front motor bearing stopper 2; 14. Coupler; 35. Inferior shell (outer body); 36. Upper shell (outer body); 38. Tube threaded lock.
Figure 17:
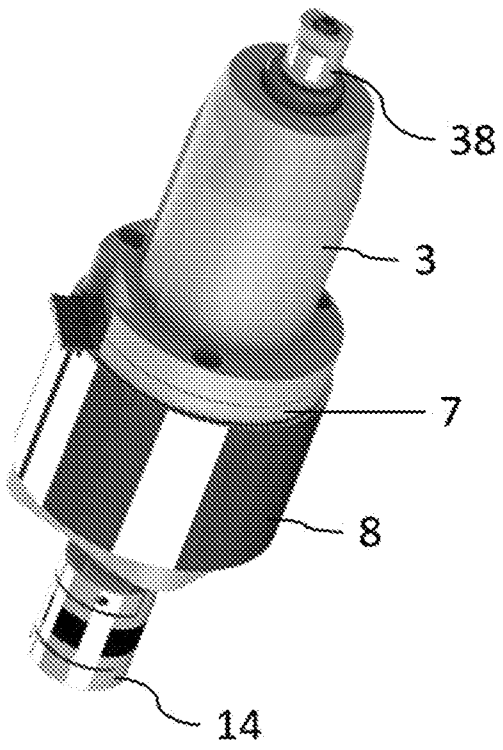
FIG. 17—Illustrates a Possible Arrangement of the extraction tool (100) wherein the reference numbers refer to: 3. Rotary Union Fixation Cover; 7. Rear Flange; 8. Motor; 14. Coupler; 38. Tube threaded lock.
Figure 18:
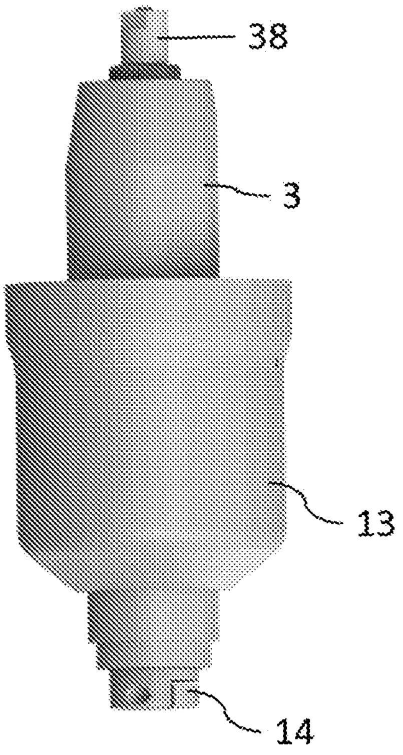
FIG. 18—illustrates a possible arrangement of the extraction tool (100) wherein the reference numbers refer to: 3. Rotary Union Fixation Cover; 13. Intermediate cover; 14. Coupler; 38. Tube threaded lock.
Figure 19:
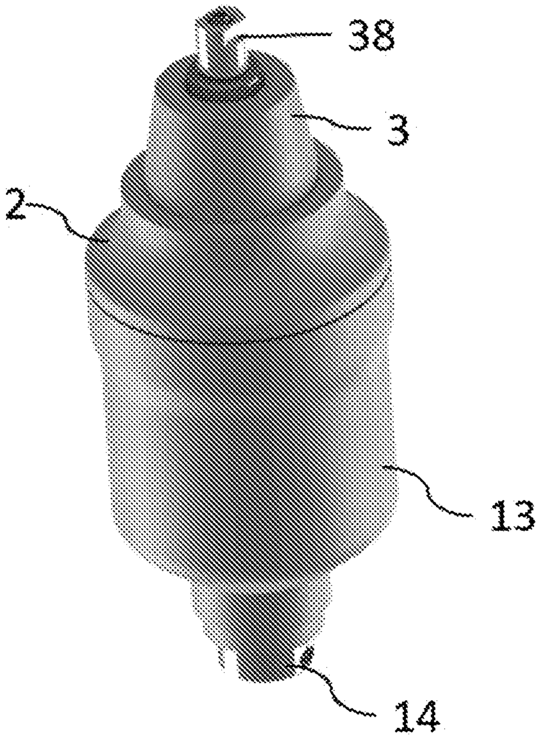
FIG. 19—Illustrates a Possible Arrangement of the extraction tool (100) wherein the reference numbers refer to: 2. Rear cover; 3. Rotary Union Fixation Cover; 13. Intermediate cover; 14. Coupler; 38. Tube threaded lock.
Figure 20:
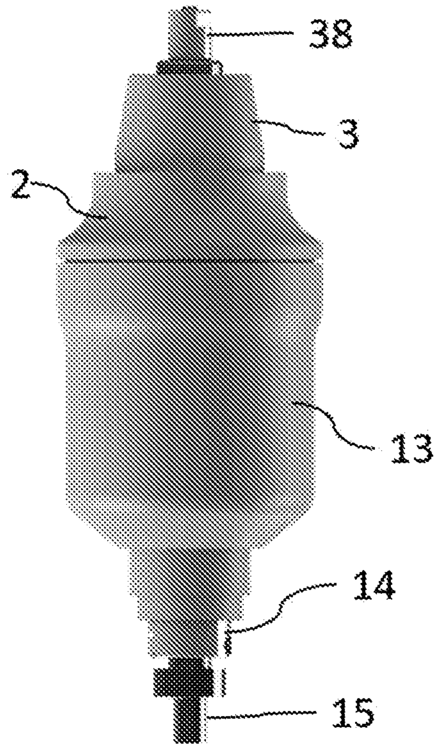
FIG. 20—Illustrates a Possible Arrangement of the extraction tool (100) wherein the reference numbers refer to: 2. Rear cover; 3. Rotary Union Fixation Cover; 13. Intermediate cover; 14. Coupler; 15. Shaft; 38. Tube threaded lock.

The tool (100) assembly requires a correct sequence that ensures its correct fitting, and consequently its subsequent operation. Thus, the Motor (8), comprising a central rotating shaft (25), will require that a set of flanges, in particular Front Flange (9) and Rear Flange (7), will be correctly bolted the outer structure of said Motor (8) accordingly to the illustration of FIGS. 7 and 8. The rotating shaft (25), as illustrated in FIGS. 7, 8 and 9, comprises a fully hollow section over its entire length. A set of motor bearings and stoppers will also be adapted to the central rotating shaft of the Motor (8), in particular a Rear shaft bearing (5) between a Rear motor bearing stopper 1 (4) and Rear motor bearing stopper 2 (6) within the Rear Flange (7) and a Front shaft bearing (11) between a Front motor bearing stopper 1 (10) and a Front motor bearing stopper 2 (12) within the Front Flange (9). Subsequently, a Coupler (14) is coupled to the rotating shaft (25) of the Motor (8), particularly adapted to said shaft (25) by fixation means and sequentially after, or in front of the Front motor bearing stopper 2 (12) located in the vicinity of the Front Flange (9). The coupler's (14) main purpose is to guarantee the physical interlocking and coupling between the punch (22) and the motor central rotation shaft (25) in order to guarantee the transmission of the rotation of the motor shaft (25) to the punch (22). The coupler (14) on one end is coupled to the motor rotation shaft (25), and on the opposite end to the punch support, or collet (20).

The rotary union (1) is mainly a mechanism that promotes the break of rotation of the shaft (25) of the motor (8), and that allows the passage of biological material and fluids from the extraction of the follicle units of a patient skin, being therefore biocompatible and autoclavable. In order to guarantee the break of rotation, in one section of the rotary union (1) there is rotation and in the opposite side there is not, allowing the shaft (25) of the motor (8) to rotate and exert the cutting force while at the other end of said union (1) there is no movement, and there can be a connection to a reservoir. The rotary union (1) will be assembled to the Motor (8) shaft by means of a threaded assembly (in one end), threaded section (31.1) of shaft (31), which additionally comprises retaining rings and sealers to ensure pressure within the vacuum circuit, and additional bearings that promote the rotation of the overall set promoted by the Motor (8) which actuates the rotating shaft (25). To note that the overall rotating set, centrally aligned with the Inner PTFE tube (23) and which runs entirely through the entire length of the hollow section of the rotating shaft (25), is completely hollow in order to allow the aspiration of the follicular unit trimmed by the tip of the punch (22), i.e., the knurled section (22.2) of punch (22), towards the Follicle Reservoir (203), which is also ensured by an additional Outer PTFE tube (24) fitted to the opposite end of the rotary union (1), like illustrated in FIG. 4, by means of an tube threaded lock (38). The rotary union (1) is comprised of a set of elements sequentially coupled together, said set being characterised by comprising a hollow central section which crosses all their lengths and which, as previously mentioned, allows the follicular units to pass through the interior of the extraction tool (100) during the suction process. The rotary union (1) is then comprised, in one end, by a threaded shaft with barbed connection (31), to which a first bearing (30) will be coupled in an opposite end where the threaded section (31.1) and barbed section (31.2) of the shaft (31) are located, and a second bearing (27) right after the first bearing (30)

between which a spacer is used (28). A spacer (26) and a seal (32) are sequentially fitted immediately after the second bearing (27), said seal (32) being designed to ensure the pressure in the air supply circuit between the outer PTFE tube (24) and the Inner PTFE tube (23). The Inner PTFE tube (23) will be adapted to the threaded shaft (31) by means of the barbed section (31.2). Above and around Shaft (31) will be applied a Lower Shell (35) that will be coupled by threaded elements to an Upper shell (36) that in turn will be located above and around the Spacer (28), the Bearing (27), the Spacer (26) and the Seal (32). The Upper shell (36), besides the threaded element at one end that allows adaptation to the Lower Shell (35), also includes, at the opposite end, a Threaded Section (36.1) and a Barbed Section (36.2). The Outer PTFE tube (24) will be adapted to the rotary union (1) by means of the Barbed Section (36.2). On the Threaded Section (36.1) a Tube Threaded Lock (38) will be fitted that will secure and tight the Outer PTFE tube (24) to the Barbed Section (36.2).

Back to the extraction tool (100) components, to mechanically adapt the Coupler (14) to the compression nut (21), that further will mechanically accommodate the punch (22), that will pierces the skin surface of the patient, additional elements will be required, particularly a shaft (15), that will be fitted to an end of the rotating shat of the motor (8) through said coupler (14), a shaft bearing (16), a nut bearing (17) and a nut seal (19), all of said components being sequentially adapted to each other like illustrated in FIGS. 1, 2, 23 and 24. The proposed set arrangement is required to ensure nor only the correct rotational performance of the punch (22), which will be fitted to the compression nut (21) by means of an collet (20) comprised therein, but also ensure the vacuum pressure inside the aspiration circuit, allowing the follicular unit to run smoothly between the punch (22), passing through the Inner PTFE tube (23) and the Outer PTFE tube (24) in direction to the Follicle Reservoir (203). The Barbed Section (22.1) of the punch (22) will promote the connection with one of the ends of the Inner PTFE tube (23), said barbed section (22.1) may comprise various geometrical shapes in order to ensure the secure mechanical fastening/adaptation with the Inner PTFE tube (23), while the opposite end of said tube (23) will be fitted to Barbed Section (31.2) of the Shaft (31). To ensure the fixation of the punch (22) to the extraction tool (100), an adaptive dimensional collet (20) is required, enclosed within the Compression Nut (21), and which will engage said punch (22). In the opposite end of the Barbed Section (22.1), the Punch (22) comprises a Knurled Section (22.2) which may have various arrangements and saw-blade layouts.

Figure 21:
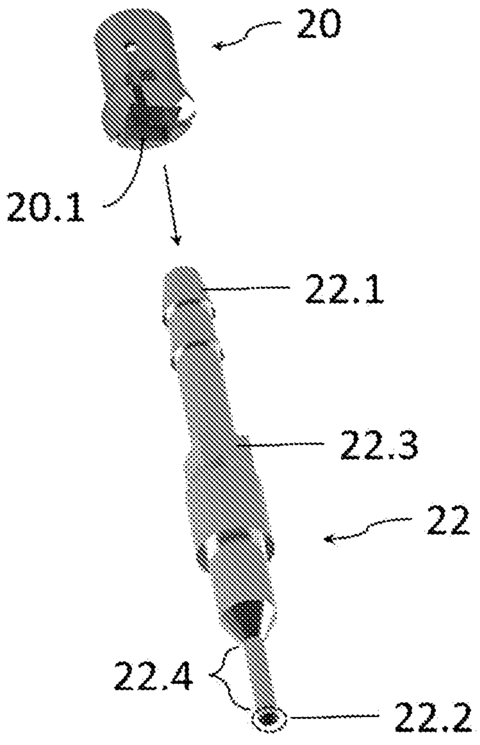
FIG. 21—Illustrates a Possible Arrangement of the extraction tool (100) wherein the reference numbers refer to: 20. Collet; 20.1. internal geometric snap-on section; 22. Punch; 22.1. Barbed section of punch (22); 22.2. knurled section of punch (22); 22.3. external geometric section; 22.4. hollow piercing section.
Figure 22:
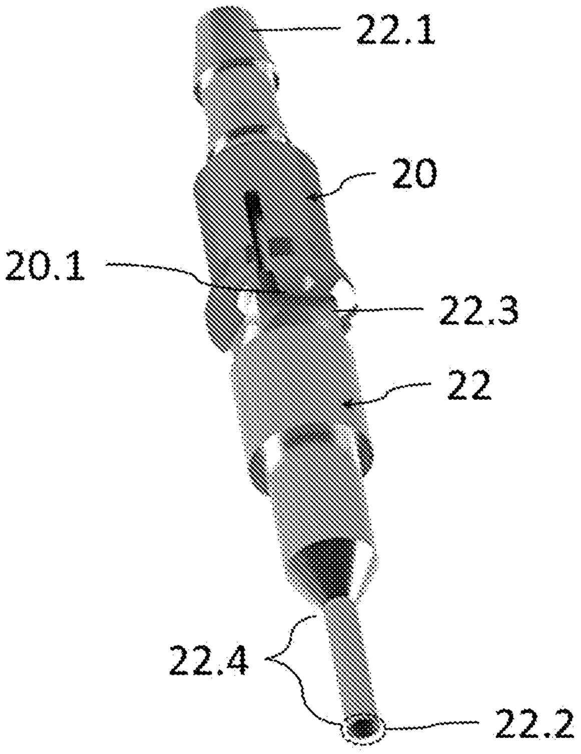
FIG. 22—illustrates a possible arrangement of the extraction tool (100) wherein the reference numbers refer to: 20. Collet; 20.1. internal geometric snap-on section; 22. Punch; 22.1. Barbed section of punch (22); 22.2. knurled section of punch (22); 22.3. external geometric section; 22.4. hollow piercing section.
Figure 23:
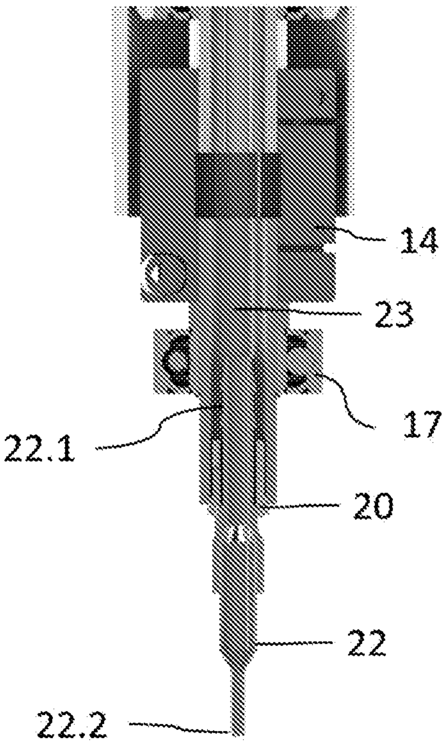
FIG. 23—Illustrates a Possible Arrangement of the extraction tool (100) wherein the reference numbers refer to: 14. Coupler; 17. Nut bearing; 20. Collet; 22. Punch; 22.1. Barbed section of punch (22); 22.2. knurled section of punch (22); 23. Inner PTFE tube.
Figure 24:
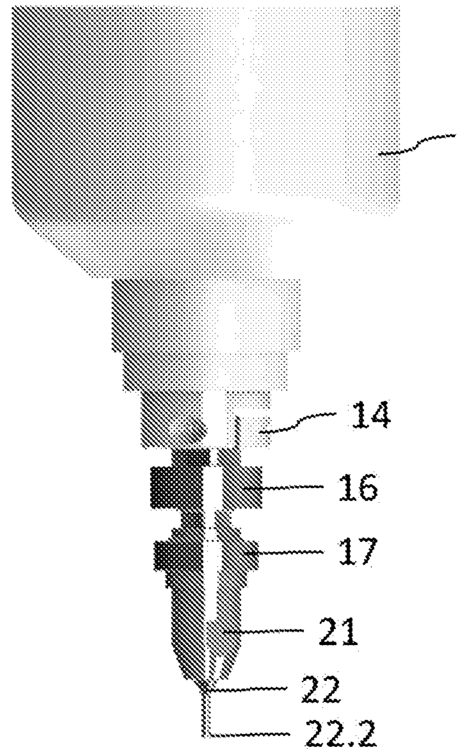
FIG. 24—Illustrates a Possible Arrangement of the extraction tool (100) wherein the reference numbers refer to: 13. Intermediate cover; 14. Coupler; 16. Shaft bearing; 17. Nut bearing; 21. Compression Nut; 22. Punch; 22.2. knurled section of punch (22).
Figure 25:
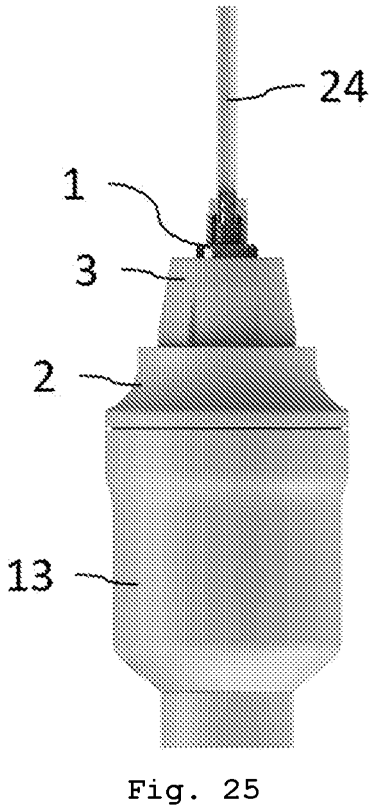
FIG. 25—Illustrates a Possible Arrangement of the extraction tool (100) wherein the reference numbers refer to: 1. Rotary Union; 2. Rear cover; 3. Rotary Union Fixation Cover; 13. Intermediate cover; 24. Outer PTFE tube.

In one of the preferred embodiments of the present invention, the punch (22) is a perforation unit—in this particular case, applicable on a skin surface—of tubular shape linearly circular and hollow in all its extension, and comprising on its external surface notches and geometric shapes which allow its coupling to a compression nut (21) by means of an adaptive dimensional collet (20), and which guarantee the transmission of the rotation features carried out by the central axis (25) of the motor (8). The punch (22) may have different hole lengths, wall thicknesses and lumens of different diameters, these being chosen according to the different needs or typologies of the follicular units to be aspirated. As illustrated on FIGS. 21 and 22, the collet (20) comprises an internal geometric snap-on section (20.1) that will be mechanically fitted to an external geometric section (22.3) comprised in the outer constructive structure of the punch (22). Both the internal geometric snap-on section (20.1) and external geometric section (22.3) are designed to mechanically fir and adapt to each other, and their geometry may comprise circular, triangular, square, hexagonal, or other identical formats, as long as they guarantee and promote an efficient and safe mechanical connection between the said parts.

The punch (22) further comprises a hollow piercing section (22.4), as illustrated in FIGS. 21, 22 and 26 to 28, with a variable number of embodiments before ending in the knurled section (22.2) which also comprises a variable number of embodiments as previously mentioned.

Figure 26:
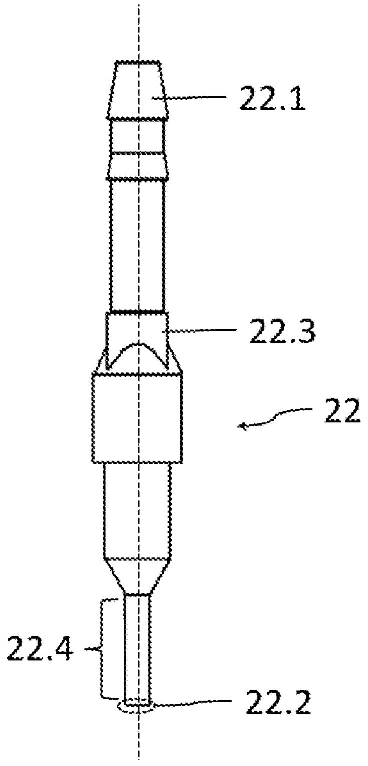
FIG. 26—Illustrates a Possible Arrangement of the extraction tool (100) wherein the reference numbers refer to: 22. Punch; 22.1. Barbed section of punch (22); 22.2. knurled section of punch (22); 22.3. external geometric section; 22.4. hollow piercing section.

In the particular case illustrated in FIG. 26, the hollow piercing section (22.4) of the punch (22) is a hollow section of uniform cylindrical shape where the opposite positioned base with regard to the knurled section (22.2) has the same diameter as the latter. Therefore, the angle of convergence of the hollow piercing section (22.4) towards the knurled section (22.2) in relation to the rotation axis of the punch (22) identified by the dashed line in the figure, is null in this particular form of realization.

Figure 27:
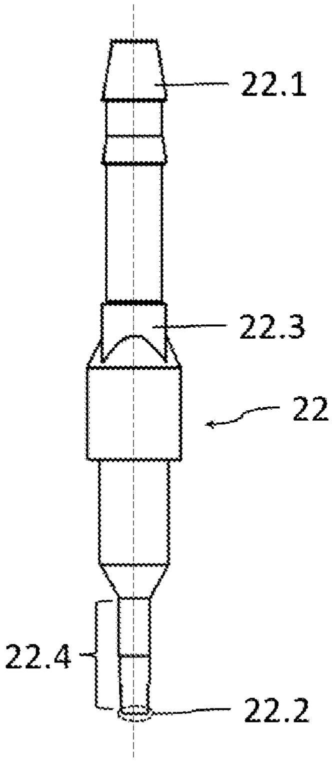
FIG. 27—Illustrates a Possible Arrangement of the extraction tool (100) wherein the reference numbers refer to: 22. Punch; 22.1. Barbed section of punch (22); 22.2. knurled section of punch (22); 22.3. external geometric section; 22.4. hollow piercing section.

In the particular case illustrated in FIG. 27, the hollow piercing section (22.4) of the punch (22) also comprises a hollow section of cylindrical shape, with a first portion linearly cylindrical and with a constant diameter, and a second cylindrical portion of diameter linearly converging towards the knurled section (22.2). This convergence results in a convergence angle of the second cylindrical portion in relation to the rotation axis of the punch (22) identified by the dashed line in said figure that may vary between 0° and 11° degrees, comprising preferential values between 1° and 50° degrees, and in an ideal realization form will be 2,29° degrees.

Figure 28:
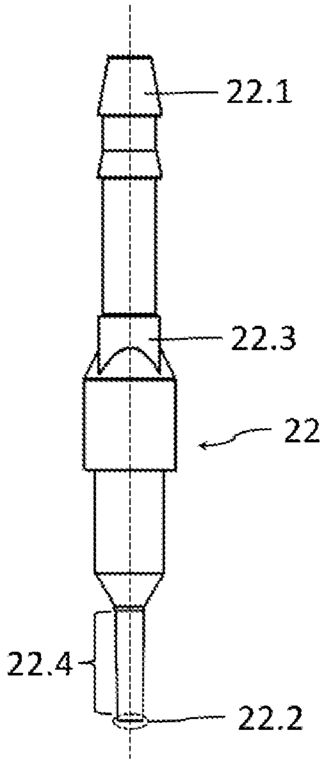
FIG. 28—illustrates a possible arrangement of the extraction tool (100) wherein the reference numbers refer to: 22. Punch; 22.1. Barbed section of punch (22); 22.2. knurled section of punch (22); 22.3. external geometric section; 22.4. hollow piercing section.

In the case illustrated in FIG. 28, the hollow piercing section (22.4) of punch (22), as previously described, also comprises a hollow section of cylindrical shape, but with a cylindrical portion of diameter linearly converging towards the knurled section (22.2). This convergence results in a convergence angle relative to the rotation axis of the punch (22) identified by the dashed line in said figure that may vary between 0° and 11°, comprising preferential values between 1° and 5°, and in an ideal realization form will be 1,18°.

Figure 2:
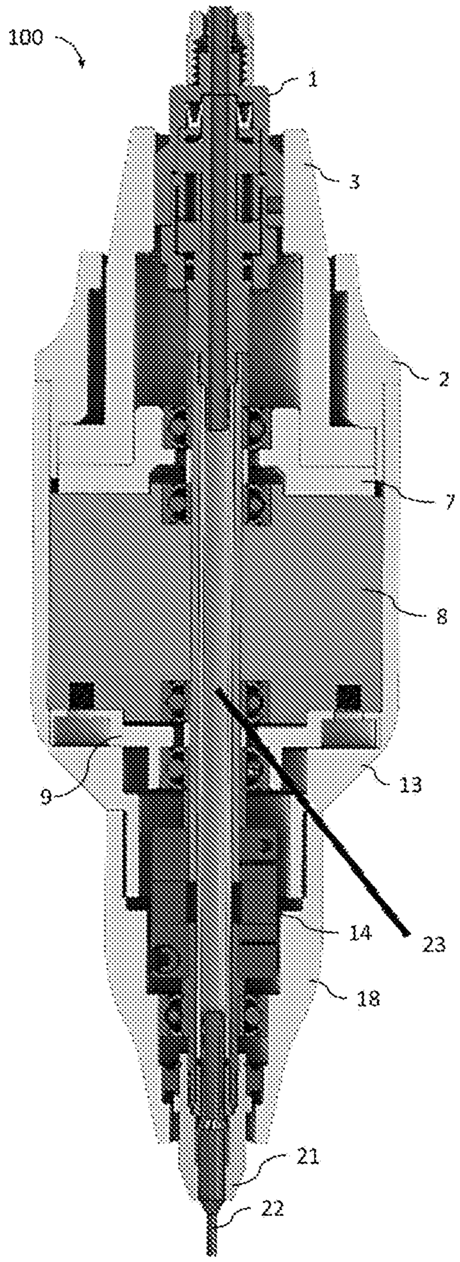
FIG. 2—illustrates a possible arrangement of the extraction tool (100) in an assembled version and in a cut-through view wherein the reference numbers refer to: 1. Rotary Union; 2. Rear cover; 3. Rotary Union Fixation Cover; 7. Rear Flange; 8. Motor; 9. Front Flange; 13. Intermediate cover; 14. Coupler; 18. Frontal cover; 21. Compression Nut; 22. Punch; 23. Inner PTFE tube.
Figure 3:
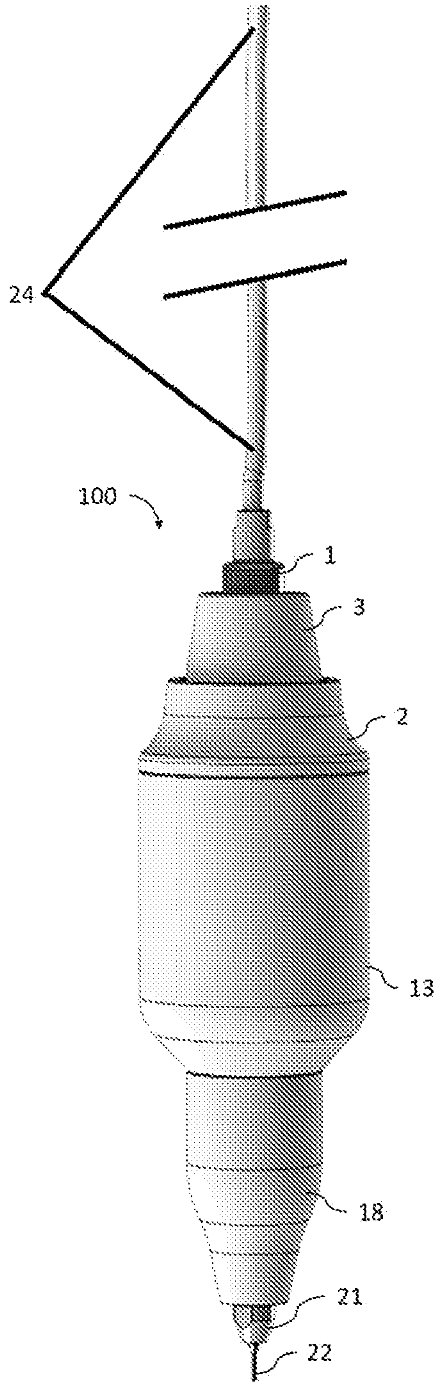
FIG. 3—illustrates a possible arrangement of the extraction tool (100) in an assembled version and in an external view wherein the reference numbers refer to: 1. Rotary Union; 2. Rear cover; 3. Rotary Union Fixation Cover; 13. Intermediate cover; 18. Frontal cover; 21. Compression Nut; 22. Punch; 24. Outer PTFE tube.
Figure 4:
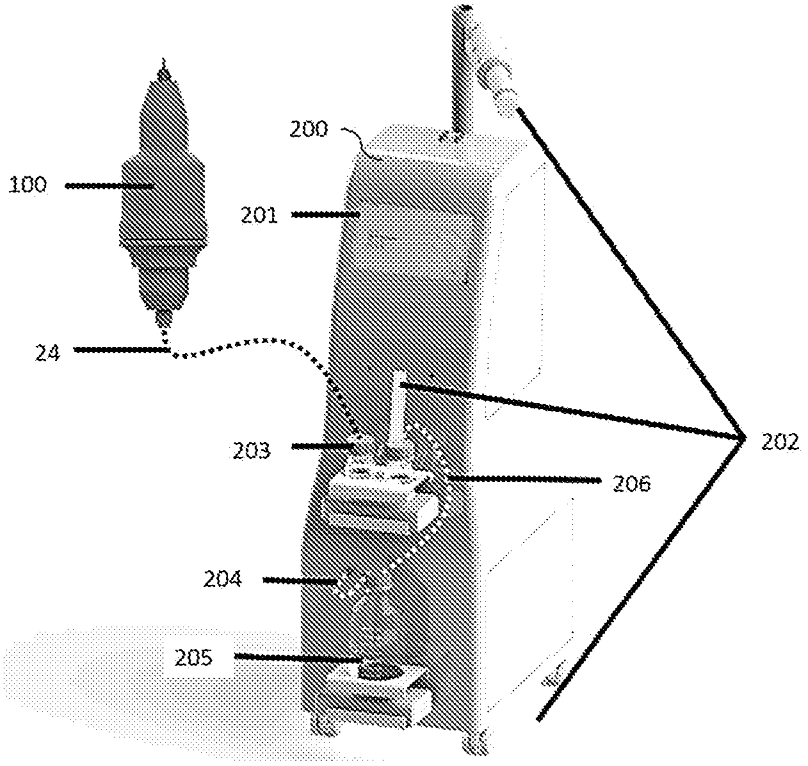
FIG. 4—illustrates a possible arrangement of the control unit (200) that ensures all the operations of the extraction tool (100) wherein the reference numbers refer to: 24. Outer PTFE tube; 201. Display; 202. Warning signaling; 203. Follicle Reservoir; 204. Tube BP; 205. Saline Reservoir; 206. Tube RB.
Figure 5:
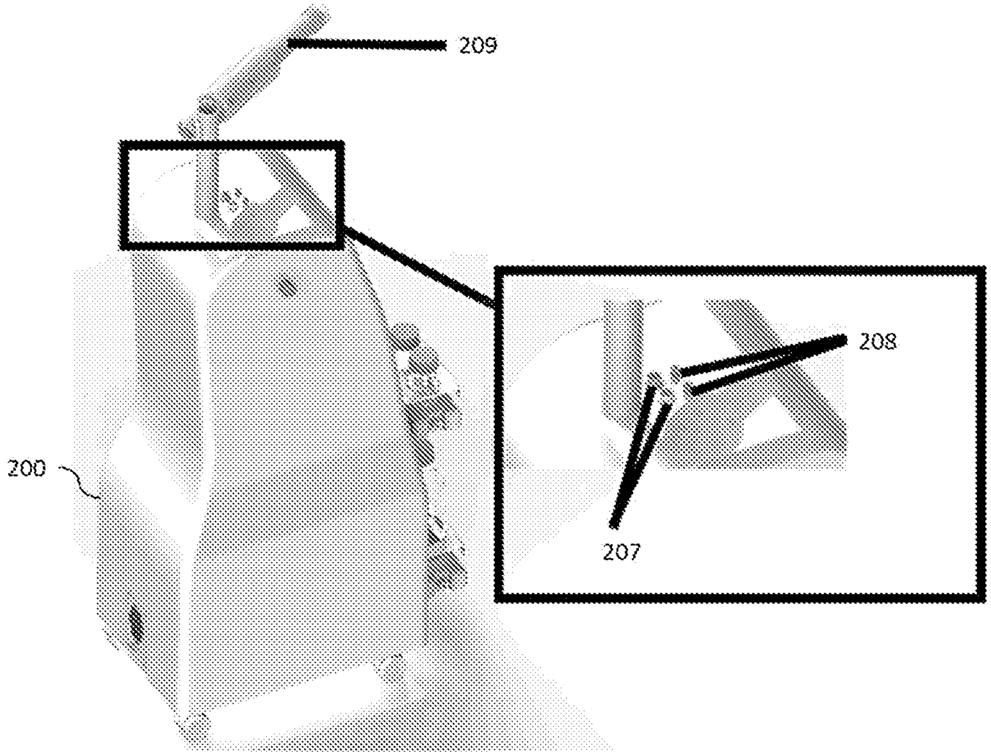
FIG. 5—illustrates a possible arrangement of the control unit (200) that ensures all the operations of the extraction tool (100) wherein the reference numbers refer to: 207. Extraction tool power connector; 208. Pneumatic connections; 209. Cable management arm.
Figure 6:
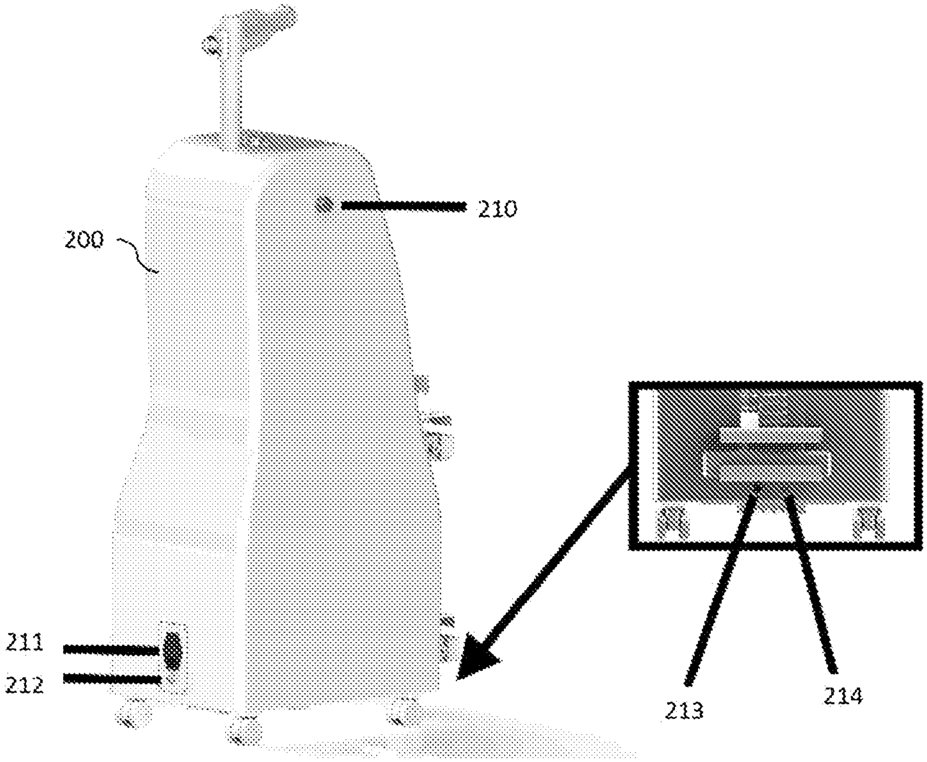
FIG. 6—illustrates a possible arrangement of the control unit (200) that ensures all the operations of the extraction tool (100) wherein the reference numbers refer to: 210. Emergency button; 211. Power supply connections; 212. Vacuum tube connections; 213. Power connection for control pedal; 214. Cable connections.

Furthermore, inside the extraction tool (100), and in order to provide the most appropriated channel for the follicle unit to travel due to the aspiration effect caused the suction pump incorporated in the control unit (200), there is an inner PTFE tube (23), which connects to the Rotary Union (1), which in turn is connected to an external outer PTFE tube (24) that leads into the Follicle Reservoir (203), as illustrated in image FIGS. 2, 3 and 4.

Both reservoirs included in the control unit (200), i.e., both the Follicle Reservoir (203) and the Saline Reservoir (205), are installed on a refrigerated location (for example over an ice cooler) which will help the preservation of the extracted follicular units from the patient by means of the tool (100).

The display (201), comprised in the control unit (200), promotes the interaction with the user of said unit (200), allowing to control and define the parameters of the extraction tool (100). To initiate the follicular extraction procedure, the control unit (200) by means of interaction with the display (201), for example a touch screen, will ask for the Patient's identification. Afterwards, and in one of the possible embodiments of the present invention, the display (201) will provide control settings that may be adjusted, and which may be related with the motor rotation speed, suction power and the graft counter sensibility. Info related with the duration of the procedure, or the number of grafts extracted from the patient is also available to the operator of the control unit (200).

In order to ensure the security of the user and the operator, the control unit (200) also comprises at least two alarm categories, utilization alarms and fault alarms. Utilization alarms represent indications of the general use of the device and are deemed to be non-critical to the patient wellbeing. Fault alarms inform for possible failures of the device, upon the appearance of said alarms the patient should be checked first and foremost, only afterwards these alarms are paused and the operator proceeds to troubleshoot eventual flaws. The diagnosis and alarm system provided within the control unit (200) allows to monitor the operational status of the extraction tool (100), allowing to assess operation failures in real time, simplifying therefore maintenance procedures once the operation issues of the equipment are identified in a timely manner. The control unit (200) is configured to report the problem that has occurred in the tool (100) and enable the equipment operator to resolve it. The precise counting of follicle units extracted is also an innovative feature since it resorts to a behavioral analysis of the motor's (8) response to the cut/perforation. While other tools on the market count the number of instructions provided by the foot control/actuator, whose accounting performance is somewhat deficient, through this development it is possible to accurately determine the number of punctures made on the skin surface thanks to the behavioral interpretation of the motor performance. Alarm priority may also vary and can be listed as a warning or an error. The Warning alarm may indicate potential critical parameters or situations that might lead to errors if not corrected. The Error alarm is related to parameters measured that lay outside the operating range, leading to stoppage of the procedure/device.

Within the alarm examples, and with particular emphasis on the Warnings, it is possible to alert for marginal motor temperature, marginal pump temperature, pump clogged or follicle count. On the Error examples, it is possible to enumerate high motor temperature, motor current peak, low motor speed, high pump temperature, pump current peak, vacuum sensor error, saline solution sensor activated and incorrect voltage.

All these errors and warnings are associated with related actions/trouble shooting procedures that aim to ease or mitigate the associated failures of the apparatus. For example, the marginal motor temperature will indicate that said motor is working near to its maximum set temperature range, and it should be monitored to stable the procedure and to proceed as normal, while the troubleshooting solution can be made at the end of the procedure. In the high motor temperature error, the motor will stop, and the procedure will require to check if any component is interfering with moveable parts. Check seals to ensure it is in its correct location. With regard to Motor current peak, it will cause the motor to stop, while the disassemble and assemble of the extraction tool will be required. In the event of low Motor speed, being its rotation below an optimal range, will lead the motor will turn off. With regard to the marginal pump temperature will require the verification if the air vents therein included are obstructed. On the other hand, if high Pump temperature is identified, said device will turn off, requiring for the verification for obstruction on the air vents. Pump current peaks will lead to a shutdown off the overall system, leading to the control unit (200) to resume the procedure in a further later stage. If a Pump clogged warning is ignited this may indicate a blockage in a section hollow section of the pressured suction system, requiring for punch verification and cleaning. If a Saline solution sensor is activated, the replacement of the Saline Reservoir (205) to ensure liquid does not enter the pump of the control unit (200). In Incorrect voltage error identified, checking if the control unit (200) is correctly turned on and the emergency button is not pressed will be required. Finally, if the Follicle count warning is triggered, the control unit (200) will emit a signaling sound every thirty executed grafts, and the device should be submerged in saline solution upon every beep.

The Follicle Reservoir (203) is the container where the extracted and aspirated follicles will be stored. It is connected to the Extraction Tool (100) through a hollow Outer PTFE tube (24). The Saline Reservoir (205), as the name hints, comprises a saline solution to preserve the follicular units extracted from the patient. Said reservoir (205) is connected to a suction pump included in the control unit (200) that ensures the vacuum in the extraction circuit and enables suction at the tip of the extraction tool (100), in particular in the tip (22.2) of the punch (22). Besides the connection to the suction pump, the saline reservoir (205) is also connected to the follicle reservoir (203), promoting the suction and circulation of the extracted follicular unit and its storing in said reservoir (203). In fact, the connections between the extraction tool (100), the Follicle Reservoir (203), the Saline Reservoir (205) and the control unit (200) through the suction pump is at least guaranteed by a hollow PTFE tube that ensures the vacuum pressure in this air circuit. Accordingly with the above, the Tube RB (206) ensures the connection between the Follicle Reservoir (203) and the Vacuum Bottle, i.e., the Saline Reservoir (205). With a similar approach, the Tube BP (204) ensures the connection between the Vacuum Bottle, i.e., the Saline Reservoir (205), and the Suction Pump (not illustrated but incorporated inside the control unit (200)). The Extraction tool power connector (207), as well as the Pneumatic connections (208), guarantee the power transmission between the control unit (200) and the extraction tool (100), as well as the continuity of the vacuum circuit between the control unit (200) and the extraction tool (100) which ensures the suction and transport of the extracted follicular units between the extraction tool (100) and the Follicle Reservoir (203).

Additionally, the operation and control of the extraction tool (100) can be performed through an additional external device, like a control pedal, that ensures its actuation.

As regards the housing of the extraction tool, being composed of several sections carefully and coupled to each other and involving the internal components of the tool (100), it can be made of various materials suitable for medical use. For example, the rotary union (1) is surrounded by the Rotary Union Fixation Cover (3), which in turn is attached to the Rear cover (2) which will be further coupled to the Intermediate cover (13) and will guarantee the involvement of the motor (8).

The invention claimed is:

1. An extraction tool to pierce a skin surface, detach and aspirate a follicular unit therein enclosed, comprising at least a motor, a circular hollow section punch and a rotary union; the motor comprises a central rotating shaft with two ends which extends beyond the dimensions of said motor at least in one first end and which will be mechanically adapted to the circular hollow section punch through a coupler; and the rotary union, comprising a first end and a second end, is coupled by its first end to the motor through the second end of the central rotating shaft, through a rear flange adapted to an outer structure of the motor and through a rotary union fixation cover that promotes the fitting and positioning of the rotary union against said outer structure of the motor; the second end of rotary union is connected to a control unit through an Outer PTFE tube; and the motor is connected to said control unit through energy and control cabling; the control unit being configured to control at least a rotation procedure of the circular hollow section punch during the skin surface piercing and detachment of a follicular unit therein enclosed and aspirate the detached follicular unit through the circular hollow punch section comprised therein towards the control unit.

2. The extraction tool according to claim 1, wherein the circular hollow section punch is mechanically adapted to the coupler at least by means of a circular hollow section shaft, a hollow section collet and a hollow section compression nut sequentially fitted together.

3. The extraction tool according to claim 1, wherein the central rotating shaft comprises a circular hollow section between the two ends extending beyond the dimensions of said motor at least in one first end.

4. The extraction tool according to claim 1, wherein the rotary union is composed by an inferior shell and an upper shell, both of said shells comprising a circular hollow section with independent bearings which are fitted to a shaft to ensure independent movement between both of said shells.

5. The extraction tool according to claim 1, wherein the upper shell comprises a barbed section and a threaded section configured to fit the Outer PTFE tube through a tube threaded lock.

6. The extraction tool according to claim 1, wherein the shaft comprises a threaded section and a barbed section.

7. The extraction tool according to claim 1, wherein the barbed section of the shaft and the barbed section of the upper shell rotate independently from each other and are internally connected through a circular hollow section.

8. The extraction tool according to claim 1, wherein the circular hollow section punch comprises a knurled section and a barbed section.

9. The extraction tool according to claim 1, wherein the circular hollow section punch comprises a hollow piercing section of cylindrical shape, said section comprising a first linearly cylindrical portion with constant diameter, and a second cylindrical portion with linearly converging diameter towards the knurled section resulting in a convergence angle with regard to a rotation axis of the punch.

10. The extraction tool according to claim 1, comprising an inner PTFE tube with a first end fitted to the barbed section of the circular hollow section punch, and a second end fitted to the barbed section of the shaft, ensuring an internal hollow circuit between the knurled section and a follicle reservoir comprised in the control unit.

11. The extraction tool according to claim 1, wherein the rotation procedure of the circular hollow section punch is provided by the rotation of the central rotating shaft therein coupled and which comprises a left or a right rotation with adjustable continuous rotational velocity.

12. A method of operating an extraction tool using the extraction tool of claim 1, comprising controlling the rotation velocity and rotation direction of the central rotating shaft of the motor; and monitoring of a set of electrical and/or data parameters in order to determine errors or faults that lead to unsafe or suboptimal performance of the extraction procedure comprising piercing the skin surface and detaching a follicular unit therein enclosed and aspirating the detached follicular unit.

13. The method of operating an extraction tool according to claim 12, wherein the control unit performing the counting of the aspirated detached follicular units based on a behavioral analysis of the motor electrical and/or data parameters in response to the extraction procedure.

14. The method of operating an extraction tool according to claim 12, wherein the extraction procedure comprising perpendicular positioning of the punch with regard to the skin surface plane while ensuring adjacent and parallel alignment between the follicular unit and the punch.

15. The method of operating an extraction tool according to claim 12, wherein the extraction procedure comprising non-perpendicular positioning of the punch with regard to the skin surface plane while ensuring adjacent and parallel alignment between the follicular unit and the punch.

* * * * *